United States Patent [19]

Callingham

[11] 4,125,600

[45] Nov. 14, 1978

[54] ANTIPERSPIRANT COMPOSITIONS

[75] Inventor: Martin Callingham, London, England

[73] Assignee: Lever Brothers Company, New York, N.Y.

[21] Appl. No.: 496,227

[22] Filed: Aug. 9, 1974

Related U.S. Application Data

[63] Continuation of Ser. No. 325,290, Jan. 22, 1973, abandoned.

[30] Foreign Application Priority Data

Jan. 28, 1972 [GB] United Kingdom ............... 4182/72

[51] Int. Cl.$^2$ .............................................. A61K 7/38
[52] U.S. Cl. ................................. 424/47; 424/67; 424/68
[58] Field of Search ...................................... 424/47

[56] References Cited

FOREIGN PATENT DOCUMENTS 1,159,685  7/1969  United Kingdom ............... 424/47
1,167,173 10/1969  United Kingdom ............... 424/47

OTHER PUBLICATIONS

Parisse, Amer. Perfumer & Cosmetics, 1971, vol. 86, pp. 46-55.

Lenthen, Amer. Perfumer & Cosmetics, 1966, vol. 81, pp. 53-57.

*Primary Examiner*—Dale R. Ore
*Attorney, Agent, or Firm*—Melvin H. Kurtz

[57] ABSTRACT

An aerosol antiperspirant composition comprising hexylene glycol as an emollient and dispersant, optionally together with a germicide and/or antiperspirant agent as active ingredients, and a base, such as an aminoalcohol to suppress the development of off-odors.

A typical formulation is:

|  | % by weight |
|---|---|
| Aluminium chlorhydrate | 3.50 |
| Hexylene glycol | 2.00 |
| Nonionic surfactant | 0.10 |
| Pyrogenic silica | 0.10 |
| 2-amino-2-methylpropan-1-ol | 0.12 |
| Perfume | 0.44 |
| Propellant 11/12 (65/35) | balance to 100 |

7 Claims, No Drawings

ANTIPERSPIRANT COMPOSITIONS

This is a continuation of application Ser. No. 325,290, filed Jan. 22, 1973, now abandoned.

This invention relates to antiperspirant compositions.

Our copending British patent application No. 39690/70 and the other applications corresponding thereto relates to an aerosol antiperspirant of the so-called 'powder' type, described in British patent specification No. 1,167,173. In nearly all powder aerosol antiperspirants a finely divided antiperspirant agent is dispersed in a medium consisting essentially of a fatty or oily substance, such as a fatty acid ester, and an aerosol propellant. However in application No. 39690/70 it is suggested that the fatty or oily substance may be replaced advantageously by hexylene glycol. Whilst the use of hexylene glycol produces an excellent antiperspirant produce in terms of the film which is deposited on skin and the ease of removal of the product when accidentally applied to clothing, we have found that such products can develop off-odours which makes them difficult to perfume.

We have now discovered that the development of off-odours in antiperspirants containing hexylene glycol can be substantially prevented by adding a base to the ingredients of the composition during manufacture.

Accordingly the present invention provides an aerosol antiperspirant composition comprising a dispersion of an acidic antiperspirant agent in a medium comprising hexylene glycol and a base.

In a second aspect of the invention there is provided a method of manufacturing an antiperspirant composition substantially free from the development of off-odours which method comprises incorporating a base into the composition during manufacture.

Without wishing to be limited to any theory, we believe that the off-odours developed by antiperspirant compositions containing hexylene glycol are caused by olefins. In particular we believe that acid catalysed elimination of water from hexylene glycol can lead to the formation of olefins and since these are more volatile than hexylene glycol their smell becomes noticeable even though they are present only in small amounts.

We consider that acid for the catalysis is produced from water present in trace amounts in the ingredients of the composition. A very small amount of the acidic antiperspirant agent (aluminium chlorhydrate for example) dissolves in this water and is subsequently hydrolysed, producing hydrogen ions.

One way of preventing olefin formation is to ensure that the ingredients used for preparing the composition are completely free from water. However, this has not proved possible when manufacturing on a commercial scale.

If, on the other hand, a base is incorporated in the composition the acidity of the trace amount of water is reduced and olefin formation is substantially prevented.

It is preferred that the base used should be a weak base such as 2-amino-2-methylpropan-1-ol (AMP), 2-amino-2-methylpropan-1,3-diol (AMPD) or monoethanolamine since the amount necessary to prevent olefin-formation is then less critical, although strong bases such as the alkali-metal hydroxides, triethanolamine and ammonia may also be used.

The amount of the base necessary to prevent olefin-formation will depend upon the acidity of the antiperspirant agent and upon the amount of water present in the antiperspirant composition, the more acid the antiperspirant agent and the greater amount of water, the greater will be the amount of base needed. The weight ratio of base to antiperspirant agent will generally be in the range of from 1:20 to 1:100 although ratios outside this range may also be used. We have found an amount of from about 0.001 to about 0.20%, more particularly 0.02 to 0.15% by weight to be a sufficient amount of base to counteract the effect of the water introduced into our composition by about 3.5% by weight of aluminium chlorhydrate.

In manufacturing the antiperspirant compositions in accordance with this invention it is quite important that the base should be added to the ingredients in the mixer at an early stage in the mixing process. It is preferred that it is thoroughly dissolved in the hexylene glycol before the antiperspirant agent is added since otherwise it is possible that local concentrations of base could occur which could react with the antiperspirant agent.

Any one of the large number of acidic materials which have been proposed for use as astringent antiperspirant agents may be used in the compositions of this invention provided that they are capable of formulation as a dispersion in the antiperspirant medium. Thus any antiperspirant agent which is soluble in the commonly used aerosol propellants referred to below is excluded from use in these compositions since it will not be capable of formulation as a dispersion.

In general, the amount of the acidic antiperspirant agent required in the compositions of the invention will be from about 0.2 to 20%, preferably 0.2 to 10%, and most preferably 2 to 7% by weight of the composition.

Astringent metal salts, and in particular aluminium salts, are preferred as the antiperspirant agents of the invention. Most preferred is aluminium chlorhydrate. Grades of aluminium chlorhydrate which we have found particularly suitable in the compositions of the invention are those sold under the trade mark "Chlorhydrol" by the Reheis Chemical Company, a Division of the Armour Pharmaceutical Company, of 111 East Wacker Drive, PO Box 1022, Chicago, Illinois. Detailed specifications of these grades are described in the booklet entitled "Chlorhydrol" published by the manufacturer in 1970.

Another antiperspirant agent which is particularly useful is zinc phenolsulphonate.

Powder aerosol antiperspirants commonly contain a bulking agent to help prevent irreversible settling of the finely-divided astringent metal salt and to ease its passage through the valve.

Any powder that is lower in bulk density than about 200 kilos per cubic meter may be used as the bulking agent, provided that it is insoluble in the liquid medium. Powders with a bulk density of 15 to 75 kilos per cubic meter are preferred.

The nature of the bulking agent is not critical to the invention. Examples of suitable bulking agents are finely-divided silicas, variously known as colloidal, fumed and pyrogenic silicas, and hydrophobic clays. Talc may also be used, as may grease-forming soaps such as aluminium stearate. Specific finely-divided silicas are: silica No. 22 referred to in U.S. Pat. No. 3,081,223, Santocel 54 (Trade Mark) manufactured by the Monsanto Company, St. Louis, Missouri; Cab-o-Sil M-5 (Trade Mark) a submicroscopic particulate silica prepared in a hot gas environment (1100° C.) by the vapour phase hydrolysis of a silicon compound and available from the Cabot Corporation, Boston, Mass.; Bentone 34, a reaction product of montmorillonite and dimethyloctadecyl ammonium chloride the latter constituting one third of the Bentone compound; and Acrosil 200, a pyrogenic silica manufactured by Deutsche Gold und Silberscheideanstalt of Frankfurt, West Germany. These bulking agents are preferably present in amounts of from 0.05 to 1.25%, more preferably 0.1 to 0.5% by weight.

Optionally the antiperspirant compositions of the invention may contain a germicide. If a germicide is included then it will be in an amount of from about 0.01 to 0.5% by weight, depending on the degree of its germicidal activity. However, we have discovered that hexylene glycol itself can provide the composition with deodorant activity and so the use of a germicide is not obligatory.

If a germicide is to be used in the compositions of the invention, we prefer to use chlorhexidine, dichlorophene, and quaternary ammonium compounds such as cetyltrimethyl ammonium bromide.

The antiperspirant compositions can contain perfumes in conventional amounts.

The compositions of this invention are dispensed from a conventional aerosol by means of a volatile aerosol propellant. In general the propellant or mixture thereof is chosen to produce a pressure of about 15 to 75, preferably about 25 to 45, and more preferably about 35 psig in the headspace of the can.

Typical of the halogenated hydrocarbons which can be used are the following compounds which have the following trade names: trichlorfluoromethane (Areton 11), dichlorodifluoromethane (Arcton 12), dichlorofluoromethane (Arcton 113) and symmetrical dichlorotetrafluoromethane (Arcton 114).

Petroleum hydrocarbons such as propane and isopropane, n-butane and isopentane may also be used.

In the process of manufacture of an aerosol powder antiperspirant composition according to the invention formulated with aluminum chlorhydrate as the astringent metal salt it is preferable to include a surfactant in the composition.

The surfactant should be both soluble in the antiperspirant medium which consists essentially of a solution of hexylene glycol in an aerosol propellant and chemically compatible with the other components of the composition. Once this requirement is satisfied the precise nature of the surfactant is not critical to the invention.

We prefer to use nonionic surfactants in the process and composition of the invention although cationic and anionic surfactants can also be used. We have found the propylene glycol/propylene oxide condensates manufactured by the Wyandotte Chemical Company and sold under the Trade Mark "Pluronic" to be suitable nonionic surfactants. Amongst these Pluronic L62D and Pluronic L64 are preferred substances. Other nonionic surfactants which we have found to be suitable are polyoxyethylene lauryl ethers, such as that sold under the Trade Mark "Brij 30", polyoxyethylene cetyl ethers, such as that sold under the Trade Mark "Brij 52", water-soluble lanolins such as that sold under the Trade Mark "Solulan 98", polyoxyethylene stearates such as that sold under the Trade Mark "Myrj 52" and the mono-fatty acid esters of ethylene oxide/sorbitan condensates such as polyoxyethylene sorbitan monolaurates, polyoxyethylene sorbitan monopalmitates, polyoxyethylene sorbitan monostearates and polyoxyethylene sorbitan mono-oleates sold under the general Trade Mark "Tween".

Amongst these cationic surfactants which are suitable for use in the process and compositions of the invention are the quaternary ammonium salts such as cetyl trimethyl ammonium bromide, stearyl dimethyl benzyl ammonium chloride, Marinol (Trade Mark), "Quaterlan C" (Trade Mark) and "Morpan E" (Trade Mark).

An alkali metal alkyl ether sulphate, such as Empicol ESB-30 (Trade Mark), an aqueous solution of sodium lauryl ether sulphate containing an average of 2 ethylene oxide units per molecule is an example of a suitable anionic surfactant.

Typical amounts of surfactant in the powder antiperspirants are from about 0.01% to about 1.5% by weight of the final product, the preferred range being from about 0.02% to 0.2% or even 0.5% by weight. Expressed another way, the surfactant should preferably be present in the slurry at a level of about 0.3 to 3% or even 10% by weight.

The invention will be further described in the following Examples.

EXAMPLE 1

This example illustrates a typical process for preparing an aerosol powder antiperspirant composition containing aluminium chlorhydrate and a formulation of such an antiperspirant.

1 part by weight of chlorhexidine, 2 parts by weight of a surfactant and 1 part of 2-amino-2-methylpropan-1-ol are dissolved in 20 parts of hexylene glycol together with the required amount of perfume. From 1 to 2 parts of Aerosil 200 are then suspended in the solution, and, after thorough mixing, 35 parts of finely divided aluminium chlorhydrate are added and mixed in to form a slurry.

A portion of the slurry formed in this way is dispensed into an aerosol unit and a propellant is added by the through-button filling method to form an antiperspirant according to the invention having the following composition:

|  | % by weight |
|---|---|
| Aluminium chlorhydrate | 3.1 |
| Aerosil 200 (a pyrogenic silica) | 0.1 |
| Hexylene glycol | 1.8 |
| Chlorhexidine | 0.1 |
| 2-Amino-2-methylpropan-1-ol | 0.1 |
| Perfume | 0.4 |
| Arcton 11 (Trichlorofluoromethane) | 61.6 |
| Arcton 12 (Dichlorodifluoromethane) | 32.6 |
| Surfactant | 0.2 |

"Arcton" is a Trade Mark.

It has been found that if a surfactant is incorporated in the slurry, as described above, it is possible to allow the slurry to stand for substantially longer periods of time prior to its being dispensed into an aerosol unit than is the case if the surfactant is omitted. We have found that if the surfactant is omitted the slurry forms a coherent mass in the bottom of the storage vessel within one or two days at the most.

Although in the above example of the process according to the invention the aerosol propellant is added to the slurry at a late stage by means of through-button filling, it will be understood that it may be added at earlier stages and by different methods without excluding the process from the scope of the invention. For example, if desired, propellants which are liquid at room temperature and pressure can be added to the preformed slurry prior to its being dispensed into aerosol cans.

The above process avoids wastage of the aluminium chlorhydrate due to formation of a coherent mass and also facilitates dispersion of the chlorhydrate in the liquid medium.

EXAMPLE 2

This example illustrates aerosol powder antiperspirant composition not including a surfactant.

|  | % by weight |
| --- | --- |
| Aluminium chlorhydrate | 3.5 |
| Aerosil 200 | 0.1 |
| Hexylene glycol | 2.0 |
| Chlorhexidine | 0.1 |
| 2-Amino-2-methylpropan-1,3-diol | 0.1 |
| Perfume | 0.4 |
| Arcton 11 | 61.0 |
| Arcton 12 | 32.8 |

EXAMPLE 3

The following experiment was performed.

A mixture of 1 part by weight of aluminium chlorhydrate and 1 part by weight of hexylene glycol was refluxed at 100° C. for 2 hours with and without the addition of 2-amino-2-methylpropan-1-ol (AMP) and of water. Samples of the liquid were taken after 1 hour and at completion of the 2 hour experiment and were examined using a gas-liquid chromatograph. In addition to the expected peaks, the graphs indicated the presence of two volatile substances A and B. The results were as follows.

| Additives to suspension | | % breakdown of hexylene glycol | |
| --- | --- | --- | --- |
| | | 1 hr | 2 hrs |
| — | A | 0.45 | 1.04 |
| | B | 0.29 | 0.05 |
| 2% Water | A | 1.44 | 3.04 |
| | B | 0.08 | 1.17 |
| 2% AMP | A | negligible | 0.03 |
| | B | 0.06 | 0.07 |
| 2% Water, 2% AMP | A | negligible | negligible |
| | B | 0.09 | 0.10 |

It can be shown that the two volatile substances A & B are the olefines 2-methyl-4-hydroxypent-1-ene and 2-methyl-1:3-pentadiene respectively and that they have objectionable off-odours.

The above experiment therefore demonstrates that the use of a base such as 2-amino-2-methylpropan-1-ol can substantially reduce the extent of formation of olefines A and B in antiperspirants containing aluminium chlorhydrate and hexylene glycol.

I claim:

1. An aerosol antiperspirant composition comprising
   (a) from 0.2 to 20% by weight of finely-divided astringent metal salt antiperspirant agent;
   (b) a liquid comprising hexylene glycol and a hydrocarbon or halogenated hydrocarbon aerosol propellant, said finely-divided astringent metal salt being dispersed in said liquid;
   (c) wherein the improvement comprises a base in an amount effective to prevent development of off-odors from said hexylene glycol; the ratio of base to antiperspirant agent being in the range of from about 1:20 to 1:100.

2. An aerosol antiperspirant composition according to claim 1 wherein the base is 2-amino 2-methylpropan-1-ol.

3. An aerosol antiperspirant composition according to claim 1 wherein the base is 2-amino-2-methylpropan-1,3-diol.

4. An aerosol antiperspirant composition according to claim 1 wherein the base is monoethanolamine.

5. An aerosol antiperspirant composition according to claim 1 wherein the antiperspirant agent is aluminium chlorhydrate.

6. An aerosol antiperspirant composition according to claim 1 comprising from 0.01 to 0.5% by weight of a bulking agent selected from the group consisting of colloidal silica, fumed silica, pyrogenic silica and hydrophobic clay.

7. An aerosol antiperspirant composition according to claim 1 comprising from 0.01 to 0.5% by weight of a germicide selected from the group consisting of chlorhexidine, dichlorophene and quaternary ammonium compound.

* * * * *